United States Patent [19]
Möckel et al.

[11] Patent Number: 6,143,326
[45] Date of Patent: *Nov. 7, 2000

[54] ORAL PHARMACEUTICAL PREPARATION CONTAINING IBANDRONAT

[75] Inventors: Jörn Möckel, Heidelberg; Rolf-Dieter Gabel, Schwetzingen; Heinrich Woog, Laudenbach, all of Germany

[73] Assignee: Roche Diagnostics GmbH, Mannheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/147,149
[22] PCT Filed: Apr. 21, 1997
[86] PCT No.: PCT/EP97/01940
§ 371 Date: Nov. 25, 1998
§ 102(e) Date: Nov. 25, 1998
[87] PCT Pub. No.: WO97/39755
PCT Pub. Date: Oct. 30, 1997

[30] Foreign Application Priority Data

Apr. 20, 1996 [DE] Germany .............. 196 15 812

[51] Int. Cl.$^7$ .................................................. A61K 9/36
[52] U.S. Cl. .......................................... 424/482; 424/480
[58] Field of Search .................................... 424/480, 482

[56] References Cited

U.S. PATENT DOCUMENTS 5,296,475  3/1994  Flesch et al. .
5,358,941  10/1994  Bechard et al. .
5,431,920  7/1995  Bechard ................................. 424/480

Primary Examiner—Thurman K. Page
Assistant Examiner—A. Berman
Attorney, Agent, or Firm—Arent Fox Kintner Plotkin Kahn

[57] ABSTRACT

The invention is directed to well-tolerated pharmaceutical compositions for oral application, containing ibandronate or a physiologically tolerable salt thereof as active substance, the administration form consisting of an active substance-containing inner portion enclosed in such fashion by a coat free of active substance that rapid release of the active substance takes place.

3 Claims, No Drawings

ORAL PHARMACEUTICAL PREPARATION CONTAINING IBANDRONAT

This is a 371 of PCT/EP97/01940 filed Apr. 21, 1997 which claims priority from German application DE19615812.5 filed Apr. 20, 1996.

The invention relates to pharmaceutical formulations of ibandronate or its physiologically tolerable salts for oral application, and to processes for producing same.

The active substance ibandronaic acid (1-hydroxy-3-(N-methyl-N-pentyl)aminopropyl-1,1-diphosphonic acid) and its salts (ibandronates), respectively, are among the class of diphosphonic acids which, in particular, are of interest in the treatment of bone diseases and particular disorders in the calcium metabolism such as hypercalcaemia, osteoporosis, tumor osteolysis or Paget's disease. In the treatment of the diseases mentioned, these active substances must be administered frequently and over a long period of time and therefore, the aim should be especially oral application in addition to intravenous application since it is the former which is more accepted by many patients.

Fundamentally, however, oral treatment is generally complicated by the well-known problems with oral tolerability of diphosphonic acids. Diphosphonic acids or their physiologically safe salts, and particularly aminodiphosphonic acids are known to give rise to irritations of the upper gastrointestinal tract (Fleisch H., Bisphosphonates in Bone Disease, Herbert Fleisch, Bern 1993, pp. 126–131). The same applies for diphosphonates which are also ingested at relatively low dosages of, e.g., less than 50 mg per single administration form. WO 93/09785 points out that the active substance risedronate ([1-Hydroxy-2-(3-pyridinyl) ethylidene]bisphosphonate), for example, may give rise to erosions and ulcerations in the upper sections of the digestive tract. Various references allude to the gastrointestinal intolerability of the active substances pamidronate (Dodwell D. et al., Biochemical Effects, Antitumor Activity and Pharmacokinetics of Oral and Intravenous Pamidronate (APD) in the Treatment of Skeletal Breast Cancer, Br. J. Cancer 62, 496 (1990)) and tiludronate (Reginster J. Y., Efficacy and Tolerability of a New Formulation of Oral Tiludronate (Tablet) in the Treatment of Paget's Disease of Bone, J. Bone Miner. Res. 9, 615–619 (1994)). In addition, it is also well-known that motility disorders may occur when swallowing the tablets and/or the tablets to be ingested get stuck due to the particular anatomic situation in the oesophagus. This may give rise to odynophagia or oesophageal strictures as well. Frequently, this is the case with elderly patients or with patients who, due to their disease, are forced to take the required tablets predominantly in a lying position.

Accordingly, in order to solve these problems, the art demanded that fundamentally, orally available administration forms be coated with a gastric juice-resistant film so that the active substance is released only subsequent to the passage through the stomach and thus, irritations of the stomach and the oesophagus would be avoided. For example, WO 95/08331 describes administration forms by which it is possible to reduce the irritating potential of alendronate and other diphosphonates in oral application.

Due to the above-described oral intolerability of diphosphonates, there has been a search for more tolerable administration forms for a number of these active substances. In particular, oral administration forms coated with gastric juice-resistant coatings have been developed in this context. Such coatings are the choice in protecting the upper sections of the gastrointestinal tract, particularly the oesophagus or the stomach, from intolerable active substances. These gastric juice-resistant coatings on solid oral administration forms dissolve only at higher pH values of about 5.5 on, so that in the acidic gastric medium, being at a pH value far below 5.5, no active substance will be released from the administration form and thus, the stomach is protected from irritations caused by the active substance. As no active substance is released in the stomach, it is possible at the same time to prevent oesophagitis or other irritations of the oesophagus caused by the refluxing gastric contents containing active substance. As a consequence, DE 59 005 517 (EP 421,921) describes a gastric juice-resistant oral administration form for pamidronate which is suitable in reducing the risk of gastric ulcerations. Furthermore, WO 93/09785 illustrates such an administration form for risedronate, WO 95/08331 for alendronate and other diphosphonates.

The potential advantages of the gastric juice-resistant administration forms are contrasted by a number of drawbacks. Thus, resorption with these administration forms may be reduced as compared to forms releasing in a pH-independently rapid fashion, or resorption is substantially more variable as compared to conventional forms, thus impairing or jeopardizing therapeutical safety. Therefore, there is a demand in alternative administration forms for these active substances in order to avoid the disadvantages of the gastric juice-resistant forms and nevertheless, be capable of providing sufficient protection from these aminobisphosphonates having aggressive effects on the gastric mucosa.

Surprisingly, it was found that improved oral tolerability in the case of the ibandronate active substance is already achieved when peroral administration forms are coated with an adjuvant coating or film in such fashion that the active substance is dissolved within a short period of time and correspondingly high local concentrations of active substance are achieved in the stomach. The film dissolving upon contact with digestive juice is preferably a coating which dissolves pH-independently. The adjuvant coating may be coated using methods common in pharmaceutical technology. Although this coating does not prevent dissolution of ibandronate in the stomach, it was surprising that no significant side effects were observed in clinical studies using ibandronate even at high dosages. Despite the fact that the administration forms are coated with a film which quickly releases the active substance, there are no irritations in the oesophagus when swallowing the tablets, and oesophagitis does not occur. This is particularly advantageous since the administration forms of the invention are also well-tolerated by patients lying in bed.

According to the invention, solid oral formulations of ibandronate are provided, consisting of a core containing the active substance, which is coated with an adjuvant coating free of active substance, which either dissolves independently of the pH value or is removed from the solid oral formulation upon contact with digestive juice. In this way, relatively rapid disintegration of the drug form and release of the active substance within a short period of time are ensured, whereby high local concentrations of the active substance are achieved. The coating may be applied using methods such as film coating, press coating, tablet coating, encapsulating or micro-encapsulating. The release of active substance from the appropriately coated solid administration forms for oral application, such as film tablets, coated tablets, laminated tablets, capsules, or microcapsules, takes place more rapidly as compared to the gastric juice-resistant administration forms. According to the invention, at least 30% of the contained ibandronate dose, but preferably at least 75% and, in particular, at least about 85% is released rapidly and independently of the pH value within the physiological pH range. Preferably, the time period required to achieve these release percentages is less than 2 hours, more preferably less than 1 hour, with about 1–30 minutes being particularly preferred. It is particularly preferred that the release is about 80–90% within a time period of up to 15 minutes. Conveniently, the release of active substance is estimated within the scope of an in vitro experiment according to well-known standardized procedures.

Surprisingly, rapid release of the active substance does not result in the undesirable side effects usually known for diphosphonic acids as described above, despite the high local concentrations of active substance (i.e., despite the high gradient of active substance) thereby generated in the stomach. Rather, it was found that despite the rapid release of active substance, the problem of occurring gastrointestinal disorders is avoided, quite surprisingly. Furthermore, it has been observed that among patients treated with such rapidly releasing administration forms of ibandronate, there were significantly less cases of nausea, vomiting, pain or diarrhoea than otherwise observed when administering aminobisphosphonates.

The coatings with rapid release of active substance in the meaning of the invention can be applied to all the suitable peroral administration forms such as tablets, capsules, coated tablets, pellets, granulates or powders. These administration forms consist of mixtures of active substances with pharmaceutical adjuvants or of pure active substances. Coating may be performed using various methods common in pharmacy. For example, suitable methods use tablet coating units, film coating units, tablet presses for press coating, encapsulating machines, or micro-encapsulating units, such as facilities for spray freezing and spray embedding, facilities for producing simple or complex coacervates.

In the meaning of the invention, pharmaceutically common or physiologically safe polymers are possible as film-forming agents. Film-forming agents in the meaning of the invention are derived from, e.g., the groups of cellulose derivatives, dextrins, starches and starch derivatives, polymers based on other carbohydrates and derivatives thereof, natural gums such as gum arabic, xanthans, alginates; polyacrylic acid, polyvinyl alcohol, polyvinyl acetate, polyvinylpyrrolidone, polymethacrylates and derivatives thereof (Eudragit®), chitosan and derivatives thereof, shellac and derivatives thereof. In addition to these film-forming agents, substances from the class of wax and fat substances may be used to produce the coatings according to the invention.

Preferably, the soluble alkyl- or hydroxyalkylcellulose derivatives such as methylcellulose, hydroxymethylcellulose, hydroxyethylcellulose, hydroxypropylcellulose, methylhydroxyethylcellulose, methylhydroxypropylcellulose, or sodium carboxymethylcellulose are possible as cellulose derivatives. In a preferred variant of an embodiment of the invention, methylhydroxypropylcellulose is employed. The usual cellulose derivatives suitable for pharmaceutical purposes, with varying degrees of substitution and/or varying molecular weights corresponding to varying viscosity levels of the aqueous solutions, may be used as suitable film-forming agents on the basis of cellulose. Likewise, insoluble cellulose derivatives such as ethylcellulose may be employed.

In the case of polymethacrylates, cationic copolymerizates of dimethylaminoethyl methacrylate with neutral methacrylic esters (Eudragit® E), copolymerizates of acrylic and methacrylic esters having a low content of quaternary ammonium groups (described in "Ammonio Methacrylate Copolymer Type A or Type B" USP/NF, Eudragit® RL and RS, respectively), and copolymerizates of ethyl acrylate and methyl methacrylate with neutral character (in the form of an aqueous dispersion, described in "Polyacrylate Dispersion 30 Per Cent" Ph. Eur., Eudragit® NE 30 D) are possible.

Similarly, the use of film-forming agents usually employed in the production of gastric juice-resistant films is possible as long as pH-independently rapid release of the active substance from the appropriately coated administration form, as described above, is ensured, e.g., by a thin layer thickness of the coating or other measures such as an extremely high percentage of pore-forming agents or the like. Anionic copolymerizates of methacrylic acid and methyl methacrylate (described in "Methacrylic Acid Copolymer, Type C" USP/NF, Eudragit® L and S, respectively, or in the form of the Eudragit® L 30 D aqueous dispersion), acidic cellulose derivatives such as cellulose acetate phthalate, cellulose acetate trimellitate and methylhydroxypropylcellulose phthalate, polyvinyl acetate phthalate, etc. may be used as such films.

In principle, all the film-forming agents may be employed alone as well as in mixtures of two or more filmforming agents.

If required, the films may contain additional adjuvants such as plasticizers, pore-forming agents, filling agents, colorants, pigments, antifoam agents, antistick agents, and the like.

According to the invention, polymers and adjuvants possibly required in addition, as were described in the preceding paragraph, are possible for press coating as far as they can be processed by means of press coating technology. In addition, all the pharmaceutically common or physiologically tolerable adjuvants which are suited to form a closed coat by press coating on the drug forms to be covered may be used in the meaning of the invention. In particular, these include adjuvants as are common in conventional tabletting, specifically filling agents from the group of carbohydrates such as lactose, saccharose, glucose and other sugars, microcrystalline cellulose, starches and starch derivatives, sugar alcohols such as mannitol, sorbitol, xylitol, inorganic filling agents such as phosphates and carbonates. According to the invention, other adjuvants as required in the production of conventional tablets, such as binding agents, disintegrants, flow agents, release agents, taste improvers, pigments, and coloring agents may be contained in addition to the filling agents.

According to the invention, all the adjuvants described above may be employed for tablet coating, in principle. In addition, special adjuvants for tablet coating may be employed according to the invention, such as palatinite, bentonite, calcium sulfate as filling agents, polyethylene glycol or polyethylene glycol fatty acid esters as release agents, colloid silicic acid as drying agent and structuring agent, magnesium oxide as spreading powder, pharmaceutically common or physiologically safe fats and waxes as glossing agents.

In the meaning of the invention, all the pharmaceutically common capsules such as gelatin hard capsules, soft gelatin capsules, starch capsules are possible as capsules. The capsules may be filled with powders, granulates, pellets or tablets. In general, all the pharmaceutically common solid, liquid and semi-solid formulations may be filled into the capsules of the invention.

For micro-encapsulating the active substance or formulations of the active substance, all the polymeric filmforming agents mentioned above may be used according to the invention. Here, the polymers may be used alone as well as in mixtures of multiple polymers, and also together with other adjuvants, if necessary.

In the following, the invention will be illustrated by way of embodiments which are not intended as limitation.

For example, The ibandronate active substance is employed in amounts of 0.1–100 mg per single dosage unit. Preferably, the dosage is at least ca. 1 mg, 5 mg, 10 mg, or 20 mg as lower limit for the amount of active substance in a single administration form. The upper limit is about 250 mg, particularly 100 mg and 50 mg, respectively.

EXAMPLE 1

| Ibandronate-containing core: Ibandronate dose [mg] in 200 mg tablet core: | 10.0 | 20.0 | 50.0 |
|---|---|---|---|
| Ibandronate-free coat [mg]: | | | |
| Methylhydroxypropylcellulose | 5.1425 | 5.1425 | 5.1425 |
| Titanium dioxide | 2.4650 | 2.4650 | 2.4650 |
| Macrogol | 1.5000 | 1.5000 | 1.5000 |
| Talc | 0.8925 | 0.8925 | 0.8925 |
| Total film coated | 10.0000 | 10.0000 | 10.0000 |

Film-coating is carried out in common apparatus. Coating conditions: tablet charge 140 kg; feed air temperature: 60° C.

EXAMPLE 2

| Ibandronate-containing core: Ibandronate dose in 100 mg tablet core [mg]: | 0.1 | 2.5 | 5.0 |
|---|---|---|---|
| Ibandronate-free coat [mg]: | | | |
| Methylhydroxypropylcellulose | 2.057 | 2.057 | 2.057 |
| Titanium dioxide | 0.986 | 0.986 | 0.986 |
| Macrogol | 0.600 | 0.600 | 0.600 |
| Talc | 0.357 | 0.357 | 0.357 |
| Total film coated | 4.000 | 4.000 | 4.000 |

Film-coating in a conventional 250 l tablet coating tank. Coating conditions: tablet charge 144 kg.

EXAMPLE 3

| Ibandronate-containing core: Ibandronate dose [mg] in 200 mg tablet core: | 10.0 | 20.0 | 50.0 |
|---|---|---|---|
| Ibandronate-free coat [mg]: | | | |
| Talc | 2.00 | 2.00 | 2.00 |
| Lactose | 1.40 | 1.40 | 1.40 |
| Methylhydroxypropylcellulose | 0.80 | 0.80 | 0.80 |
| Titanium dioxide | 0.80 | 0.80 | 0.80 |
| Macrogol | 0.40 | 0.40 | 0.40 |
| Ethyl methyl methacrylate copolymer* | 0.04 | 0.04 | 0.04 |
| Polysorbate | 0.04 | 0.04 | 0.04 |
| Total film coated | 5.48 | 5.48 | 5.48 |

*Employed in the form of Eudragit ™ NE 30 D as an aqueous dispersion.

Film-coating in a conventional 15 l tablet coating tank. Coating conditions: tablet charge 13.0 kg.

EXAMPLE 4

| Ibandronate-containing core: Ibandronate dose [mg] in 86 mg tablet core: | 10 |
|---|---|
| Ibandronate-free coat [mg]: | |
| Saccharose | 37.844 |
| White clay | 8.138 |
| Talc | 1.000 |
| Macrogol | 2.848 |
| Glucose syrup | 2.035 |
| Titanium dioxide | 1.628 |
| Polyvidone | 0.407 |
| Montan glycol wax | 0.100 |
| Total tablet coating applied | 54.000 |

Tablet coating in a conventional 15 l tablet coating tank with dip pipe.

EXAMPLE 7

| Ibandronate in laminated tablet | |
|---|---|
| Ibandronate-containing core: | |
| Final weight: | 86 mg |
| Format of core: | 7 mm in diameter, plane, with facettes |
| Ibandronate dose in tablet core: | 10 mg |
| Ibandronate-free coat: | |
| Lactose | 270 mg |
| Microcrystalline cellulose: | 90 mg |
| Pressing tool: | 12 mm in diameter |
| Final weight of laminated tablet: | 446 mg |

Pressing by means of a hand press using conventional procedures.

What is claimed is:

1. A method of treating a bone disease in a patient in need thereof, comprising orally administering to the patient a pharmaceutical formulation comprising a tablet core containing about 0.1 to 100 mg of ibandronate and a coating which is free of ibandronate and has the following proportional composition:

(a) about 51.425% by weight of methylhydroxypropylcellulose;

(b) about 24.650% by weight of titanium dioxide;

(c) about 15.000% by weight of polyethylene glycol; and (d) about 8.925% by weight of talc.

2. The method of claim 1, wherein the bone disease is related to a disorder in calcium metabolism.

3. The method of claim 1, wherein the bone disease is selected from the group consisting of hypercalcemia, osteoporosis, tumor osteolysis, and Paget's disease.

* * * * *